United States Patent [19]

Lampropoulos et al.

[11] Patent Number: 5,711,302
[45] Date of Patent: Jan. 27, 1998

[54] DISPOSABLE TRANSDUCER WITH DIGITAL PROCESSING AND READOUT

[75] Inventors: Fred P. Lampropoulos, Sandy; Don C. Kartchner, West Jordan; Steven R. Taylor, Salt Lake City, all of Utah

[73] Assignee: Merit Medical Systems, Inc., South Jordan, Utah

[21] Appl. No.: 205,321

[22] Filed: Mar. 3, 1994

[51] Int. Cl.$^6$ ..................................................... A61B 5/02
[52] U.S. Cl. .......................... 128/672; 128/670; 128/696; 128/748
[58] Field of Search ..................................... 128/672, 673, 128/674, 675, 690

[56] References Cited

U.S. PATENT DOCUMENTS

| | | |
|---|---|---|
| 4,227,420 | 10/1980 | Lamadrid ................................ 128/675 |
| 4,245,648 | 1/1981 | Trimmer et al. ...................... 128/672 |
| 4,347,851 | 9/1982 | Jundanian ............................. 128/672 |
| 4,398,542 | 8/1983 | Cunningham et al. ................. 128/675 |
| 4,404,974 | 9/1983 | Titus .................................... 128/672 |
| 4,539,998 | 9/1985 | McCoro et al. ....................... 128/675 |
| 4,557,269 | 12/1985 | Reynolds et al. ...................... 128/675 |
| 4,610,256 | 9/1986 | Wallace ................................ 128/675 |
| 4,658,829 | 4/1987 | Wallace ................................ 128/675 |
| 4,679,567 | 7/1987 | Hanlon et al. ......................... 128/675 |
| 4,817,629 | 4/1989 | Davis et al. ........................... 128/748 |
| 4,825,876 | 5/1989 | Beard .................................... 128/675 |
| 5,086,777 | 2/1992 | Hishii ................................... 128/675 |
| 5,218,970 | 6/1993 | Turnbull et al. ....................... 128/748 |
| 5,273,047 | 12/1993 | Tripp et al. ........................... 128/675 |

OTHER PUBLICATIONS

NAMIC® Perceptor™ DT Brochure, July 1991.

*Primary Examiner*—Jennifer Bahr
*Assistant Examiner*—Stephen Huang
*Attorney, Agent, or Firm*—Workman, Nydegger, & Seeley

[57] ABSTRACT

A self-contained battery operated disposable blood pressure monitor having a semi-conductor transducer therein, the front side of which is intended to be fluid communication with an incompressible fluid in a intracorporeal catheter inserted in the heart of a patient for direct blood pressure monitoring. A calibration port vents the backside of the transducer to calibration and atmospheric pressures. The monitor contains circuitry electrically connected to the transducer which receives electrical signals output by the semi-conductor chip in response to the pressures exerted upon it through the pressure monitoring port. The circuity then electronically processes the signals so as to derive electronic data representing the mean arterial pressure pulse rate, and both systolic and diastolic blood pressures. The circuitry also analyzes the pressure wave forms of the pressure signals detected for poor signals so that it can present a visual diagnostic representative of the problematic pressure condition.

25 Claims, 6 Drawing Sheets

Microfiche Appendix Included
(1 Microfiche, 95 Pages)

DISPOSABLE TRANSDUCER WITH DIGITAL PROCESSING AND READOUT

A portion of the disclosure of this patent document contains material to which a claim of copyright protection is made. The copyright owner has no objection to the reproduction by anyone of the patent document or the patent disclosure as it appears in the United States Patent and Trademark Office patent file or records, but reserves all other rights with respect to the copyrighted work.

Exhibit A, referred to herein, may be found in the microfiche appendix contained in the Patent and Trademark Office file for this document. The microfiche appendix is comprised of one (1) microfiche having ninety-five (95) frames.

BACKGROUND

1. Field of the Invention

The present invention relates to pressure monitors for medical use. More particularly, the present invention relates to self-powered disposable devices which display a monitored physiological pressure and incorporate a pressure transducer capable of calibration, the monitored physiological pressure including direct measurement of blood pressure by use of an indwelling catheter and the like.

2. Prior State of the Art

One of the most frequently measured conditions of a patient undergoing an evaluation, diagnosis or treatment is the patient's blood pressure. There are generally two types of methods used for measuring and/or monitoring blood pressure, namely, indirect blood pressure measurement, and direct blood pressure measurement. Indirect blood pressure measurement techniques are based on non-invasive procedures such as using a pressure cuff and a stethoscope. Direct blood pressure measurement techniques, on the other hand, are made by using invasive techniques which permit intracorporeal measuring and monitoring of blood pressures.

Notably, when diagnosing and treating critically ill patients, direct blood pressure measurements are almost always preferred over indirect blood pressure measurements due to several factors. First, use of direct blood pressure measurement greatly increases the accuracy of the blood pressure reading. Second, direct measurement facilitates the continuous monitoring of a patient's blood pressure as opposed to intermittent monitoring. Third, direct blood pressure measurement enables rapid detection of any change of cardiovascular activity, which may be of particular importance in emergency situations. Fourth, direct blood pressure measurement can also readily be used to measure and monitor a patient's blood pressure at specific internal locations, such as within the chambers of the heart. Because of these and other advantages, therefore, direct blood pressure measurement and monitoring has become a routine procedure in treating critically ill patients.

Direct blood pressure measurement and monitoring typically involves catheterization. A hollow needle or cannula is first inserted into a peripheral blood vessel. For example, in the case of monitoring arterial blood pressure, it is inserted into a radial artery. If venous blood pressure is to be monitored, the needle is inserted into the antecubital, radial, tubular or subclavian vein. A catheter is filled with a sterile saline solution and de-bubbled. The catheter is then threaded through the needle and into the particular blood vessel. The catheter may then be guided along the blood vessel until the tip of the catheter is positioned at a particular point within the body at which it is desired to make the blood pressure measurement. With the catheter thus in place, the needle may be withdrawn and the entry site of the catheter is taped down.

Prior to positioning an end of the indwelling catheter within the patient as described above, the other end of the catheter is connected to pressure tubing that in turn is connected to a pressure transducer. The catheter is generally also connected to a suitable continuous flush device or heparin drip to prevent clotting around the tip of the catheter. The pressure transducer is in turn electrically connected to a monitor and/or other output devices near the patient's bedside which display the patient's blood pressure wave form using analog and/or digital readouts.

When setting up the blood pressure measurement system as described above, it is important to prime the catheter and the tubing with the sterile solution in a way so that any air bubbles within the catheter and tubing are removed, thus providing a continuous fluid column that runs from the tip of the catheter to the pressure transducer. Then, when the catheter is positioned within the patient's blood vessel, as the patient's heart pumps blood, periodic pressure pulses are transmitted through the patient's blood vessel and along the incompressible fluid column in the catheter to the pressure transducer.

The transducer generates electrical signals representing the pressure pulses, and those signals are then amplified and displayed on the appropriate monitor and/or output devices. Usually, in such a system a display monitor is used to show the patient's blood pressure as a function of time. This type of display is commonly referred to as the blood pressure wave form. This blood pressure wave form is used by medical personnel to appropriately diagnose and treat the patient.

If an indwelling catheter is improperly placed, or if an air bubble is entrained within the incompressible fluid column, the blood pressure exerted upon the incompressible fluid column will be inaccurate. Detection by health care personnel of such inaccuracies are difficult when the blood pressure wave form or its digital equivalent is simply displayed and no analysis is being performed upon the blood pressure wave forms that are being detected by the pressure transducer.

One of the most important components of the above-described blood pressure monitor system is the pressure transducer. Significantly, the accuracy and the precision of the pressure transducer set an upper limit to the quality of the blood pressure data which can be obtained. Accordingly, pressure transducers for this type of application have been developed which have a high degree of reliability, sensitivity and accuracy. Typically, transducers for this type of application are comprised of piezoresistive semiconductor integrated circuits or "chips." These transducers have a thin diaphragm which, on one side, is in fluid communication with the sterile fluid column contained in the catheter and tubing. This thin diaphragm is deflected by the pressure pulses which travel through the fluid column in the catheter and tubing. As the diaphragm is flexed by virtue of the pressure pulses, the electrical resistance of the diaphragm changes in proportion to the amount by which the diaphragm is flexed, and appropriate electronic circuitry generates an electrical signal representing the pressure exerted on the diaphragm. In this way, the blood pressures are transformed into a suitable electrical signal or wave form.

In order to assure accuracy of pressure measurement, the transducer should be calibrated at a zero pressure by a process called "zeroing." Zeroing a transducer is important in that falsely reported pressures will yield inaccurate data that is unreliable for purposes of evaluating and/or diagnosing a patient's condition. Calibrating a transducer may be done frequently, depending on the reliability of the particular transducer being used. Reliability is affected by the transducer's propensity to produce drift or change in its output signals incident to stress from excess pressure or from thermal changes.

Transducers can be calibrated from either the front or the back side, the front side being the side that is in fluid communication with the sterile fluid column of the catheter and tubing. The back side is the side of the transducer diaphragm that is not in contact with the sterile fluid column. By exerting a known positive pressure on the front side, a display device can be read to determine if the transducer is reading at the known pressure. Conversely, by exerting a known negative pressure or vacuum on the back side of the transducer, an effect equivalent to a known positive pressure on the front side is achieved, and again, the display device can then be read. In either technique, the accuracy and need for calibration is judged by the degree of deviation of the actual transducer pressure reading as compared to the applied and known pressure. Adjustments to the monitor can then be made as necessitated and dictated by the reading, to calibrate the transducer.

There are various difficulties and hazards with calibrating a transducer by using the front or patient side that is in direct contact with the sterile fluid column that is intravenously situated in the patient. Ordinarily, calibration is done by an instrument that introduces pressure to the transducer by a fluid medium such as air.

Difficulties and hazards of patient side calibration arise from the potentiality for entry of air and/or contaminants into the patient's intravenous system. The entry of air and contaminants are a potential cause of embolisms and infection. Thus, it is desirable to avoid transducer calibration on the patient side of the transducer.

Also known in the art is back side, or non-patient side, calibration. Backside calibration avoids the undesirable aspects of patient side calibration by means of applying negative pressure to the back side of the transducer, which is isolated from the intravenous fluid column. Back side vacuum pressure is equally effective as patient side positive pressure for calibrating the transducer, while avoiding the complications of non-sterility and air emboli, which are known hazards in front side calibration techniques.

One type of back side calibration apparatus is disclosed in U.S. Pat. No. 4,610,256 to Wallace. A cable electrically connects a pressure transducer to a microprocessor, which in turn numerically quantifies the signals output from the transducer. In addition to electrically conductive wires, the cable has an air space running along its length for communication of vacuum pressure through the cable to the backside of the transducer, for the purpose of effecting calibration of the transducer. While the Wallace disclosure uses backside calibration to avoid the aforementioned hazards inherent to patient side calibration, Wallace is not without drawbacks in its disclosed technique.

The cable used to introduce the negative calibration pressure is one source of such drawbacks in that such a cable is expensive to manufacture. The cost of manufacturing mitigates against the economics required of items intended to be deposed of after use. In addition to the manufacturing expense, the cable is also generally difficult to manufacture. Further, attachment of the cable to the transducer is manually difficult, in that if the cable is secured too tightly the air space provided through the cable may be altogether pinched off, thus precluding the backside pressure required for calibration. Thus, to avoid this result, the cable connection must be loosely connected. Of course, a loosely connected cable in itself has inherent problems. Should the cable be inadvertently bumped, pulled upon or jarred, the electrical connection to the transducer can be disrupted.

The electrical cable poses additional drawbacks when the patient must be moved. To move a patient away from conventional blood pressure monitors, for instance where the patient needs to be transported, the monitor and/or other output device used to display the patient's directly measured blood pressure must first be disconnected from an electrical cable prior to transporting the patient. During transportation, or other such period of disconnection from a pressure display monitor, an undesirable 'black-out' period exists during which there is neither direct blood pressure monitoring nor any display thereof. Thus, the hemodynamic well-being of the patient, as is best known by direct monitoring and display, will be unavailable for examination during the black-out period.

When multiple patient pressures are to be monitored, such as hemodynamic, interuterine, and intercranial pressures, additional monitors may be required. Space considerations become relevant when several different physiological pressures are being simultaneously monitored due to the amount of space taken up by the number of pressure monitors required. Thus, it would be an advance in the art to provide a self-powered physiological pressure monitor that takes up a small space relative to contemporary pressure monitors.

BRIEF SUMMARY AND OBJECTS OF THE INVENTION

The present invention seeks to overcome the above described difficulties and disadvantages which have been experienced in the prior state of the art, and seeks to realize a number of important objects and advantages so as to further advance the state of the art in connection with direct blood pressure monitoring techniques, and specifically in connection with portable self-contained disposable blood pressure monitors. Briefly summarized, the principal objects and advantages of the invention are as follows.

An important object of the present invention is to provide a disposable pressure monitoring device that can be used to monitor and display physiological pressures that are normally constant, such as intracorporeal compartmental pressures, while also being capable of use to monitor and display hemodynamic pressures including mean arterial pressure (M.A.P.), pulse rate, and blood pressure.

Another important object of the present invention is to provide a disposable pressure monitoring device that is self-contained in that it is self-powered and does not require an outside power connection or an electrical cable.

A further object of the present invention is to provide a self-powered pressure monitor that is small in size relative to contemporary pressure monitors so that multiple patient pressures can be simultaneously monitored by several of the inventive pressure monitors, which pressure monitors take up comparatively less room than would a similar number of contemporary pressure monitors.

It is another important object of the present invention to provide a disposable pressure monitoring device that monitors blood pressure in direct fluid communication with the circulatory system of a patient.

Another important object of the present invention is to provide a disposable pressure monitor that accumulates hemodynamic pressure data, performs diagnostic routines on the accumulated data so as to detect abnormal pressure conditions represented by the data, and then to inform attendant health care personnel by visually outputting a representation of the data both in terms of related numerical displays and by indication of the result of the diagnostic routines performed on the data.

One important object of the present invention is to provide a disposable pressure transducer that has a housing which contains the transducer and wherein the housing is designed so as to be easily and quickly connected to a mechanism which can be used to apply a negative calibration pressure to the backside of the transducer diaphragm, rather than applying a calibration pressure through a permanent outside cable.

Another related object of the present invention is to provide a disposable pressure transducer with a housing which can be connected to standard calibration apparatus without the need for specialized interconnection parts.

Yet another important object of the present invention is to provide a housing for a disposable pressure transducer that provides a calibration port for connection to standardized calibration equipment used for applying a negative calibration pressure to the backside of the transducer diaphragm, and wherein the transducer housing can be easily and comfortably strapped to a patient's arm or mounted to an organizer on an IV pole without causing any encumbrance due to the calibration port.

Still a further important object of the present invention is to provide a transducer housing that has a calibration port through which negative calibration pressure can be applied to the transducer diaphragm which is so designed and placed on the transducer housing in a way that minimizes the potentiality of any liquids entering the port and rendering the transducer inoperative by subjecting the backside of the transducer diaphragm to any such liquids.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, it is briefly summarized that the foregoing objects and advantages of the present invention are realized in a disposable pressure transducer apparatus. The apparatus has a housing that is formed from top and bottom members that are joined together. The top and bottom members of the housing together provide a transducer chamber and also a fluid passageway for containing a pressurized fluid, the pressure of which is to be monitored. A pressure monitoring port provides communication of fluid pressures in the fluid passageway to the transducer chamber.

A semi-conductor transducer chip is disposed in the transducer chamber. The semi-conductor chip has a diaphragm formed on the chip for sensing the fluid pressures. The front side of the diaphragm senses fluid pressures through the fluid pressure monitoring port and is hermetically sealed in the transducer chamber. The transducer chip that is preferably used in the present invention is the same or similar to the transducer disclosed in the U.S. Patent Application titled "TRANSDUCER HOUSING WITH A CALIBRATION PORT", commonly owned with the present application and filed on Mar. 10, 1993 and having U.S. patent Ser. No. 08/028,997, which is incorporated herein by reference.

The housing of the apparatus also provides a calibration port which is used for purposes of venting the backside of the transducer diaphragm to atmospheric pressures and which is also used to introduce calibration pressures to the backside of the transducer diaphragm. The calibration port is formed in the bottom member of the housing. It is preferable that a small pinhole be placed in the bottom of the calibration port to serve for communicating the atmospheric pressures or calibration pressures to the backside of the transducer diaphragm. The calibration port is also hermetically sealed so that the backside of the transducer diaphragm will communicate only through the pinhole to atmospheric or calibration pressures. The calibration port and pinhole placed in the bottom of the calibration port are designed so as to minimize seepage of any liquids through the calibration port to the backside of the transducer.

The housing also has therein an electronic circuit which is electrically connected to the semi-conductor chip. The electrical circuitry in the housing is like or is similar to that which is disclosed in U.S. patent Application Ser. No. 07/664,587, titled TOTALLY SELF-CONTAINED, DIGITALLY CONTROLLED, DISPOSABLE SYRINGE INFLATION SYSTEM, AND METHOD FOR MONITORING, DISPLAYING AND RECORDING BALLOON CATHETER INFLATION DATA, and filed on Mar. 4, 1991, which is incorporated herein by reference.

The circuitry receives electrical signals output by the semi-conductor chip in response to the pressures exerted upon it through the pressure monitoring port. The circuity then electronically processes the signals so as to derive electronic data representing the physiological pressures of the patient to whom the fluid passageway is in fluid communication with. Such physiological pressures may be an intracorporeal compartment having a constant pressure therein, such as a catheterized intramuscular compartment of a patient. Alternatively, the physiological pressures may be hemodynamic pressures in a catheterized circulatory system of a patient.

After the circuitry has processed the electrical signals from the semi-conductor chip, a digitized form of the signals may then be displayed on a control panel located within the housing. The display on the control panel is electrically connected to the circuitry so that a visual display of the physiological pressures of the patient may be output.

In order that the pressure monitor disclosed herein be self-contained and independent of outside power sources, a battery is included within the housing for supplying electrical power to the semiconductor chip, the circuitry and the display on the control panel. While a battery is preferable other power means, such as one or more solar energy cells, could be similarly employed.

When the hemodynamic pressures of the patient's circulatory system are being monitored, the electronic circuitry in the housing performs diagnostic analysis on the wave forms of the pressure signals detected at the semiconductor chip. Such analysis entails derivation of mean arterial pressure (M.A.P.), pulse rate, and both systolic and diastolic blood pressures.

In addition to the aforementioned conventional hemodynamic data, the circuitry analyzes the wave forms of the pressure signals detected at the semi-conductor chip to determine if a poor signal is being detected. Poor signals occur in a variety of situations, such as air in the catheter line to the housing, or improper intracorporeal catheter installation. Upon detection of such poor pressure signal wave forms, health care personnel are alerted to such detection by the display on the control panel which will present a visual diagnostic representative of the problematic pressure condition. Similar means of alert, such as audible alarms with or without the described visual diagnostic are also contemplated as being equivalents.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PRESENTLY PREFERRED EMBODIMENTS

The present invention can best be understood by reference to the drawings, in which like parts are designated with like numerals throughout.

Figure 1:
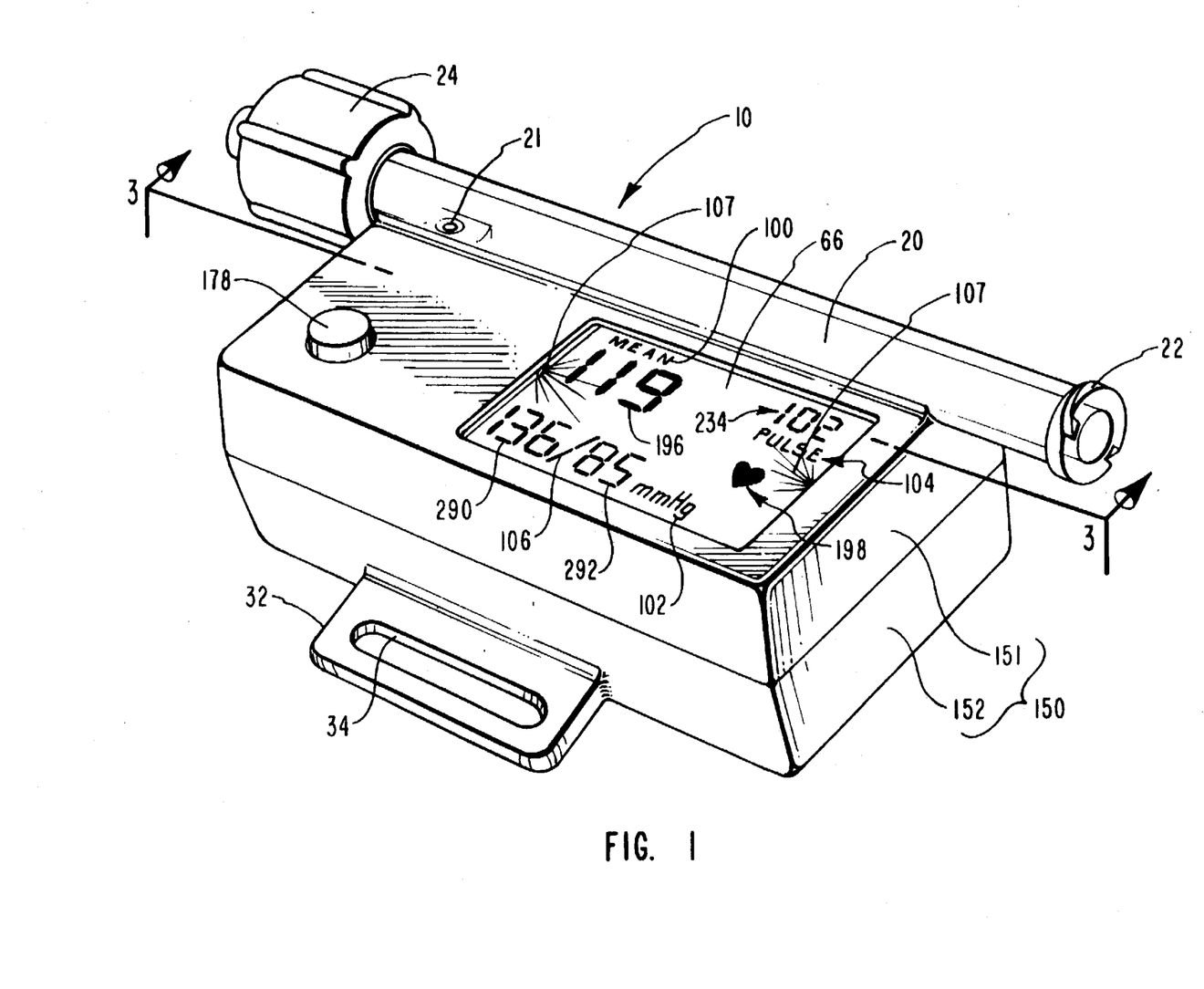
FIG. 1 is a perspective view of the presently preferred embodiment of the disposable blood pressure monitor.

Reference is first made to FIG. 1 which illustrates in perspective view a presently preferred embodiment of the present invention. FIG. 1 shows an assembled disposable pressure monitor 10 from the top side thereof. A housing 150 comprises an upper housing assembly 151 jointed to a lower housing assembly 152.

The fittings 22 and 24 provide for coupling of pressure monitor 10 to pressure tubing (not shown) of a type which is commonly known and used in the art in connection with hemodynamic blood pressure monitoring systems or other similar types of pressure monitoring systems. In the case of hemodynamic blood pressure monitoring systems, a luer fitting 24 will typically be connected to a catheter (not shown) which is inserted into the patient for purposes of either arterial or venous blood pressure monitoring.

As will be appreciated by those of skill in the art, while the present invention as illustrated and described is particularly useful for direct blood pressure monitoring, the pressure monitor 10 of the present invention is not intended to be limited to that use and may be used in connection with other types of medical pressure monitoring applications. For instance, the catheter (not shown) connected at luer connector 24 could be in fluid communication with a physiological pressure such as an intracranial pressure, intraosteal pressure, and the like. Pressure monitor 10 could be used in compartmental pressure syndrome analysis and in discograms. The artisan will understand other applications for the present device.

A display panel 66 is provided with a single control button 178, as hereinafter more fully described, which is used to activate pressure monitor 10, and which is also used to activate the back lighting lamps 107 for illumination of displayed digital data on pressure monitor 10.

Figure 2:
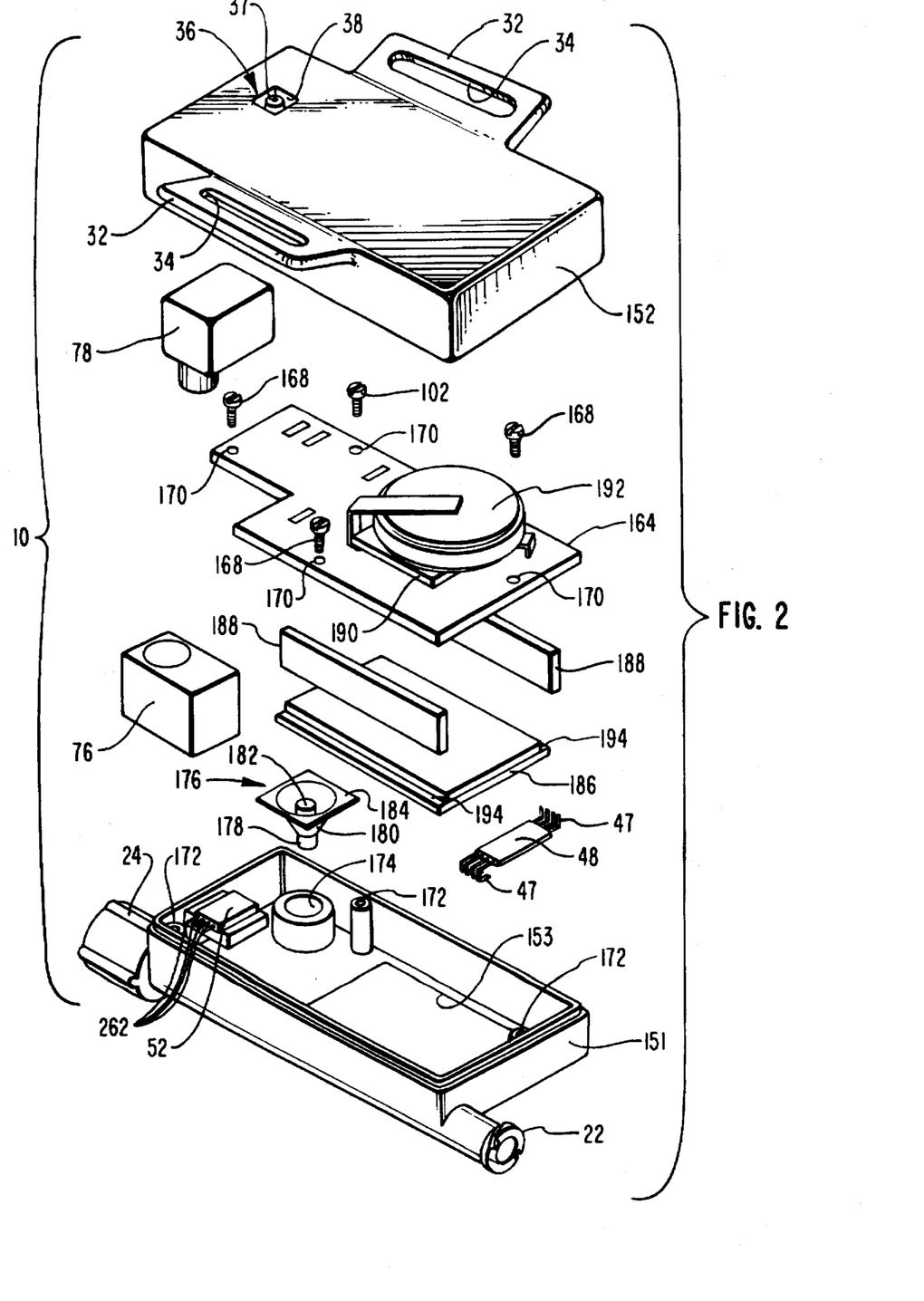
FIG. 2 is an exploded view, seen from the underside, of the embodiment of the device shown in FIG. 1.
Figure 3:
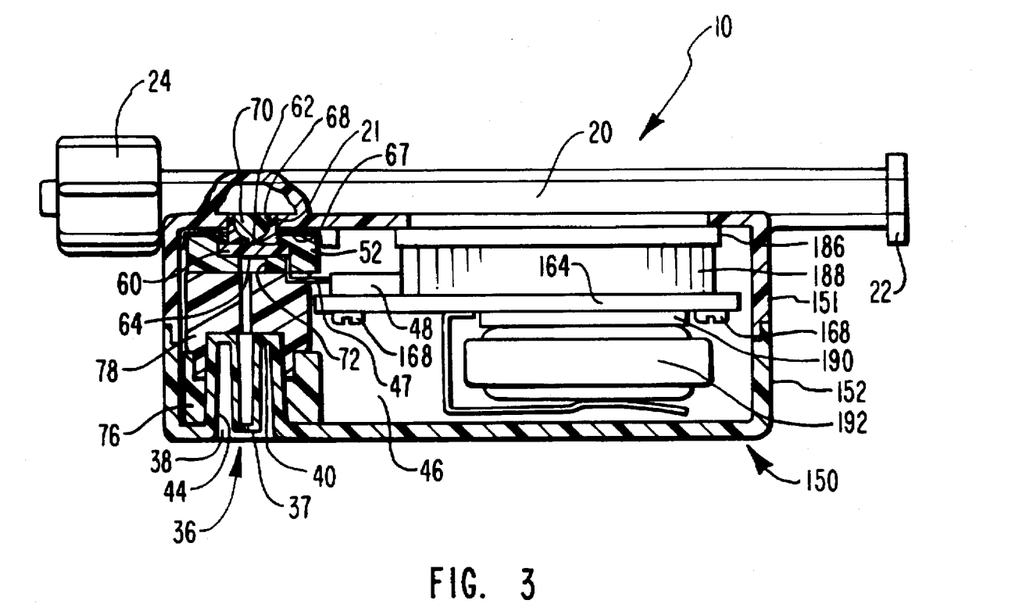
FIG. 3 is a cross-sectional view, taken along line 3—3 of FIG. 1.

The manner in which pressure monitor 10 is constructed is more particularly illustrated in reference to FIGS. 2 and 3, taken together. Housing assembly 150 is made by firmly bonding together upper housing 151 and lower housing 152. Upper housing 151 preferably has a corresponding rectangular shape to lower housing 152.

As shown in FIG. 2, lower housing 152 is preferably formed as a single molded plastic part. Lower housing 152 is formed as a generally square-shaped box having side members 32 and slots 34 attached thereto which permit pressure monitor 10 to be strapped onto the arm, leg, or other parts of a patient (not shown). Pressure monitor 10 can also, however, be mounted onto what is known in the art as a transducer organizer (not shown) which is mounted on an IV stand (not shown) for applications where several transducers are required to be used in the course of a medical procedure.

As best shown in FIG. 3, a transducer element 60 is disposed in a transducer chamber 46 to serve as an example and illustration of a transducer means for providing electric signals proportional to fluid pressure sensed, where such sensing is shown for the fluid passageway of a tube 20 through the pressure monitoring port provided by an opening 21. In the preferred embodiment, the transducer means is comprised of a piezoresistive semiconductor integrated circuit or chip. The transducer element 60 includes electronic components which form a transducer. The transducer element 60 also includes a diaphragm that is flexed by the pressure pulses and which, as schematically shown, has a front side 62 and a back side 64.

As shown in FIG. 3, transducer element 60 is in turn mounted on a chip carrier member 52 and is electrically connected to the wires 47 provided in a cable 48. Cable 48 is securely bonded in electrical communication with one side of a printed circuit board 164.

With continued reference to the sectional view in FIG. 3, chip carrier member 52 includes a bowl-shaped member 68 that fits within opening 21 of the pressure monitoring port. Bowl-shaped member 68 is filled with a well-known silicon gel material 70 which is commonly used in the art to provide electrical isolation so that front side 62 of the transducer diaphragm does not come into contact with the liquid contained in tube 20. Silicon gel material 70 that is disposed within bowl-shaped member 68 in effect serves as an isolation means for electrically isolating transducer element 60 while also providing a fluid coupling with respect to the pressure pulses that are sensed through the fluid column in tube 20. Chip carrier member 52 is hermetically sealed to upper housing assembly 151 by means of a suitable adhesive 67 or by other equivalent means such as ultrasonic bonding or the like. In this way, front side 62 of the diaphragm of transducer element 60 is hermetically sealed off from transducer chamber 46 so that front side 62 of the diaphragm of transducer element 60 can only communicate with the sensed fluid pressures in the fluid passageway defined by tube 20 through opening 21 of the pressure monitoring port.

Bowl-shaped member 68, adhesive 66, and gel material 70 serve as an example to illustrate an aspect of the invention which comprises a first hermetic sealing means for creating an airtight seal so that the front side of the transducer diaphragm is in fluid communication only with fluid pressure sensed through the pressure monitoring port.

Bowl-shaped member 68 has a small aperture which is positioned directly over front side 62 of transducer diaphragm 62 so that front side 62 of the diaphragm is in communication with the sensed fluid pressures by means of silicon gel material 70 which, in turn, is in direct contact with the fluid column in tube 20.

The pressure monitor apparatus is also comprised of a calibration port means for providing a vent to atmosphere and for providing communication of calibration pressure to the backside of the diaphragm of the transducer. An example to illustrate such calibration port means is a calibration port 36 shown in the cross-sectional view of FIG. 3. In particular, calibration port 36 is formed as a well in bottom housing assembly 152. The well has tapered cylindrical sides 44 and a bottom 40 and an open top 38. Located in bottom 40 of the well is a male projection 37 at the top of which is provided a small hole through which calibration or atmospheric pressures are communicated to backside 64 of the diaphragm of transducer element 60.

Bottom 40 of the well is spaced from the backside of chip carrier member 52 by a spacer 78. Chip carrier member 52 has a small opening 72 formed in the back side of chip carrier member 52 which communicates with back side 64 of the diaphragm of transducer element 60. Accordingly, back side 64 of the diaphragm is, in this manner, vented to atmosphere by means of opening 72, bottom 40, and the aforementioned small hole in male projection 37.

Not only is back side 64 of the diaphragm vented to atmosphere in this way, but calibration pressures are also communicated to back side 64 of the diaphragm by providing a negative or positive calibration through female calibration port 36.

Male projection 37 is desirable because fluids that enter calibration port 36 at opening 38 are less likely to flow into the small hole in male projection 37 due to its height above bottom 40. However, male projection 37 may be omitted if proper care is observed against the entry of fluids through opening 38 of calibration port 36.

Second hermetic sealing means is provided for creating an airtight seal so that the back side of the transducer diaphragm is in fluid communication only with the calibration port. This hermetic seal may be provided in a variety of ways, one presently preferred way being illustrated in FIGS. 2 and 3 by the combination of spacer 78 and elastomeric cylinder or block 76. Thus, elastomeric block 76 makes an airtight seal with back side 64 of the diaphragm of transducer element 60 so that it can only communicate with the atmospheric or calibration pressures that are introduced through calibration port 36 and opening 72.

Spacer 78 surrounds calibration port 36 at the inside of transducer chamber 46. As also shown, elastomeric block 76 is sealingly compressed between spacer 78 and bottom block 40 of calibration port 36. Elastomeric block 76 is constructed, for example, of silastic, and is dimensioned so that it will partly fit around the outside surface of side walls 44, thereby providing the aforementioned hermetic seal. Back side 64 of the diaphragm of transducer element 60 is completely hermetically sealed off from transducer chamber 46, so as to allow communication of pressure through calibration port 36. However, alternative ways of hermetically sealing back side 64 of the diaphragm can also be accomplished, for example, by hermetically sealing with an adhesive or other suitable bonding method.

The presently preferred embodiment of the pressure monitoring apparatus is digitally controlled by electronic circuit means which processes signals transduced by the transducer means so as to derive electronic data representing the physiological pressures of the patient. A power means supplies operational electrical power to the transducer means, the electronic circuit means and the display means. In the presently preferred embodiment, by way of example and the illustration in FIGS. 2 and 3, the electronic circuitry means is printed circuit board 164 which contains a microprocessor 190 and a battery 192 which are used to provide power to the electronic circuitry components. Battery 192 serve as an example and illustration of the power means, which may assume other and equivalent forms such as a solar cell or a solar cell that recharges a battery.

A conductive rubber member 188 is a material that is known in the art and is sometimes referred to as a "zebra" or "Z" strip. Accordingly, conductive rubber Z strip 188 serves to illustrate an example of a means for providing an electrical interconnection between printed circuit board 164 and a digital readout such as a LCD 186.

Figure 5:
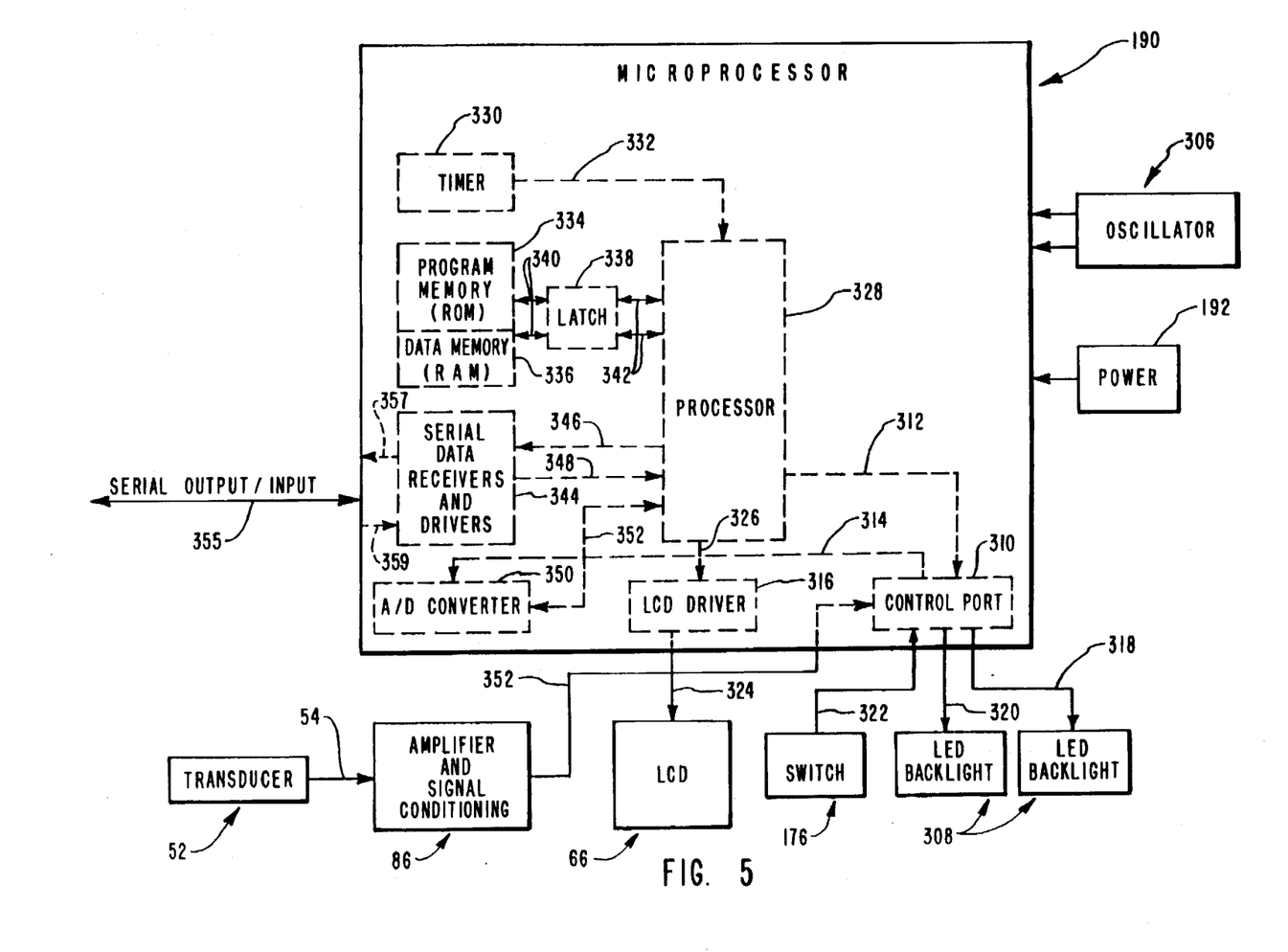
FIG. 5 is a functional block diagram which schematically illustrates the primary components of the digitally controlled electronic circuit used in connection with the disposable blood pressure monitor of FIG. 1.

With further reference to FIGS. 2 and 3, housing assembly 150 carries printed circuit board 164 onto which is mounted, as noted above, microprocessor 190, battery 192, LCD 186 as well as other electronic components which are required for the circuitry of pressure monitor 10, as detailed in the functional block diagrams of FIG. 5.

With particular reference to FIG. 2, upper housing assembly 151 has a transparent window 153 formed in the upper surface through which, LCD 186, serving as an example of the display means, may be viewed. Preferably, except for window 153, upper and lower housing assemblies 151, 152 are molded from opaque plastic material.

FIG. 2 depicts a resilient control switch 176 which is comprised, for example, of an elastomeric button switch. Switch 176 has control button 178 that extends through an opening in well 174 which is formed in upper housing member 151 so that control button 178 can be finger-actuated by pressing. Switch 176 has an integral conically-shaped skirt 180 which terminates in a generally square-shaped electrically conductive base 184. Base 184 entirely covers a portion of printed circuit board 164 so that when housing assembly 150 is complete, switch 176 is fluid tight and will thus not permit water, saline solution or other liquids to enter housing assembly 150 through the location of control button 178. The fluid tight aspect of switch 176 is due to the sealing contact between skirt 180 and well 174.

Base 184 extends downwardly and rests against the upper side of the printed circuit board 164 so that control button 178 is held in a position which extends through the opening of well 174 in upper housing assembly 151 into the position as shown in FIG. 1, but at the same time skirt 180 also seals well 174. When control button 178 is pushed downwardly, the base 182 of control button 178 is pushed into contact with a conductive path of parallel traces (not shown) on the upper side of printed circuit board 164, thereby making the necessary electrical contact to activate the electronic components, as hereinafter more fully described. The elastomeric properties of conical skirt 180 will return control button 178 upwardly when it is released.

With continued reference to FIGS. 2 and 3, microprocessor 190 is mounted to the underside of printed circuit board 164 and battery 192 is mounted over microprocessor 190 on the same side of printed circuit board 164. The upper side of printed circuit board 164 carries conductive pads (not shown) which are electrically connected to LCD 186 by means of conductive rubber Z strips 188, each of which vertically supports LCD 186 so that it is held into engagement with upper housing 151 of housing assembly 150. The channels 194 are adapted to receive the upper edge of conductive rubber Z strips 188 to provide electrical contact at LCD 186.

In the preferred assembly of housing assembly 150, control switch 176 is placed into well 174, LCD 186 is positioned over window opening 153, conductive rubber Z strips 188 are positioned at the side edges of LCD 186 in corresponding longitudinal channels 194, and then printed circuit board 164 is placed over the top of all those components. The pins 168 are then inserted through corresponding holes 170 in printed circuit board 164 and into corresponding receiving holes 172 in upper housing assembly 151. Pins 168 are bonded or otherwise anchored into holes 172 such as by a press fit or other appropriate means.

Figure 4:
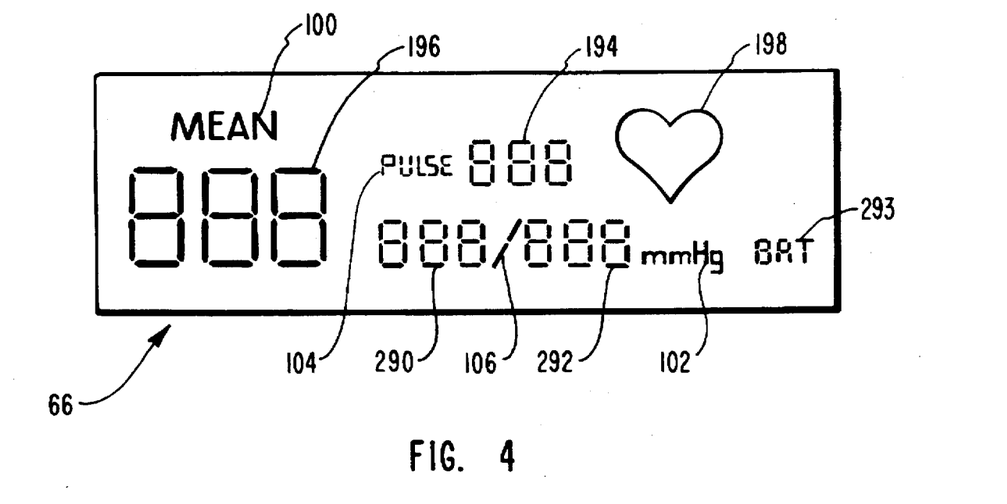
FIG. 4 is a plan view of an alternative embodiment of the digital display of FIG. 1.

The nature of the information displayed on display panel 66 is best illustrated in FIGS. 1 and 4. As schematically illustrated in those drawing figures, indicia is circumscribed thereon as described more fully below.

An indicia 100, "MEAN" signifies digital data 196 which is meant to represent the mean pressure sensed by the transducer means. Preferably, digital data 196 will be an average over a predetermined period of time of sensed pressures.

An indicia 104 marked as "PULSE" represents digital data 194 which is meant to represent the pulse rate of a patient. Preferably, the pulse rate is the timed duration between systolic peaks in the pressure of the blood in a patient.

Digital data 290 and digital data 292 respectively represent the systolic and diastolic pressures of the blood of a patient. An indicia 106 is a conventional division symbol meant to separate the digital systolic, and diastolic readouts. Additionally, an indicia 102 "mmHg" is meant to indicate that the systolic and diastolic pressures are read out in millimeters of mercury.

A conventional heart-shaped symbol 198 cyclically illuminates with each heartbeat of the patient and turns off between heartbeats.

As stated, the electronic circuit means receives signals from the transducer means from which it then derives electronic data representing the physiological pressures of the patient. When the physiological pressures of the patient are those of a circulatory system, and more particularly hemodynamic pressures, the electronic circuit mean controls display panel 66 to reflect the hemodynamic data in the form of pulse rate 194, mean pressure 196 and systolic and diastolic pressures 290, 292, in combination with heart-shaped symbol 198 which flashes with each heartbeat.

The empirical method for accurately depicting the numerical data displayed on display panel 66 from pressure sensed by transducer element 60 is not limited to any specific algorithm. It will be appreciated that the computing device of the pressure monitor could be a wide variety of computing devices. By way of example, and not by way of limitation, microprocessor 190 may be a four (4) bit N.E.C. 75328 microprocessor. Microprocessor 190 could be programmed so as to implement derivation algorithms using any one of a variety of different programming languages and programming techniques. Attached hereto as Exhibit A is one such program in source code listing, which was prepared for use with microprocessor 190 and the circuit configuration as illustrated in FIG. 5.

The electronic circuit means preferably comprises means for amplifying the electrical signal output by the transducer means, means for converting the amplified signal from analog to a digital form, digital processor means for processing the digital form of the signal so as to derive therefrom digital data which represents the physiological pressures, data memory means for storing the digital data derived by said digital processor means, and program memory means for storing machine-readable instructions utilized by the digital processor means to derive, store, retrieve and display the digital data.

Figure 6:
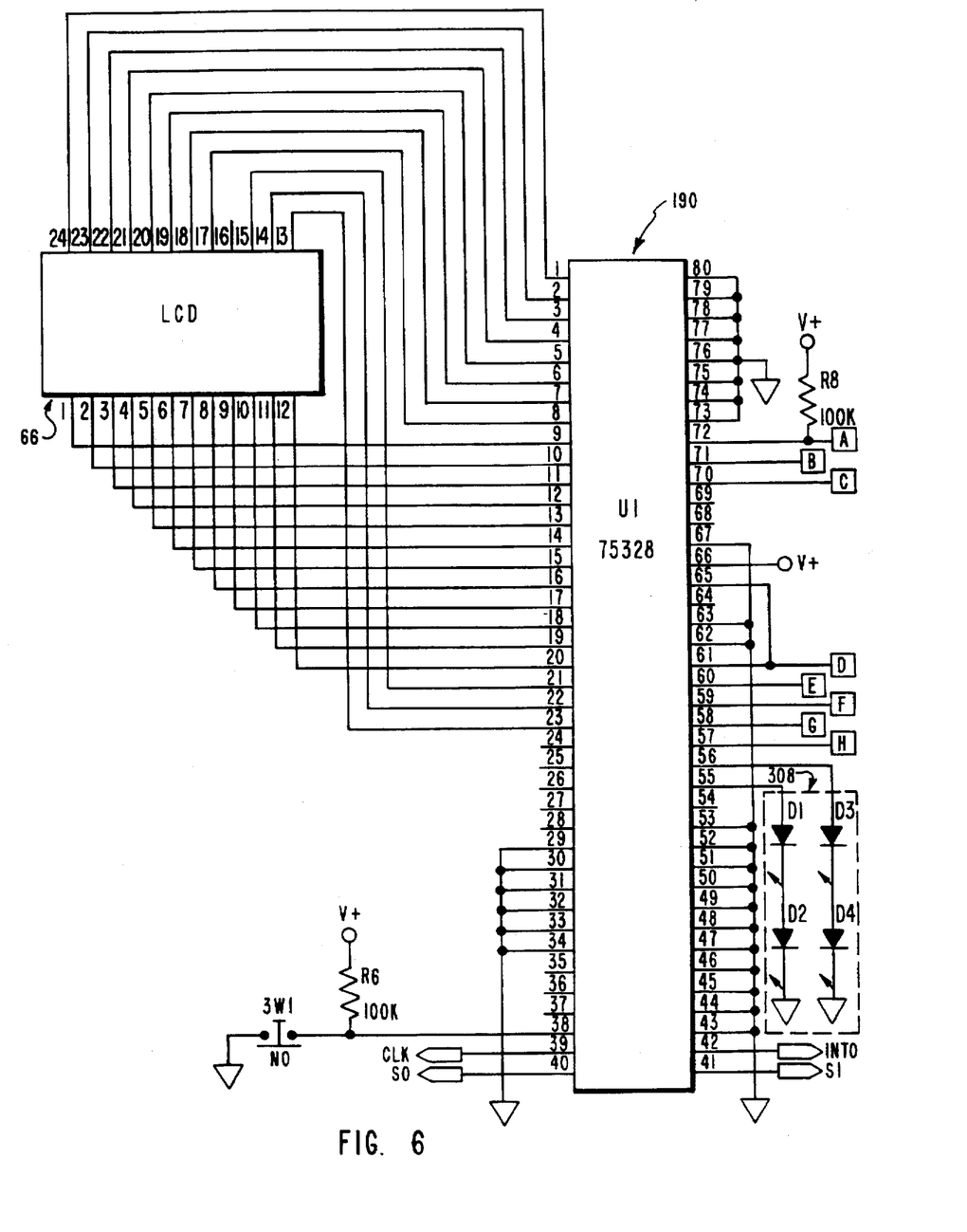
FIGS. 6 and 7 taken together constitute a detailed electrical schematic diagram which illustrate, as an example, the presently preferred embodiment and presently understood best mode for implementing the electronic circuit means of the blood pressure monitor system of FIG. 1.
Figure 7:
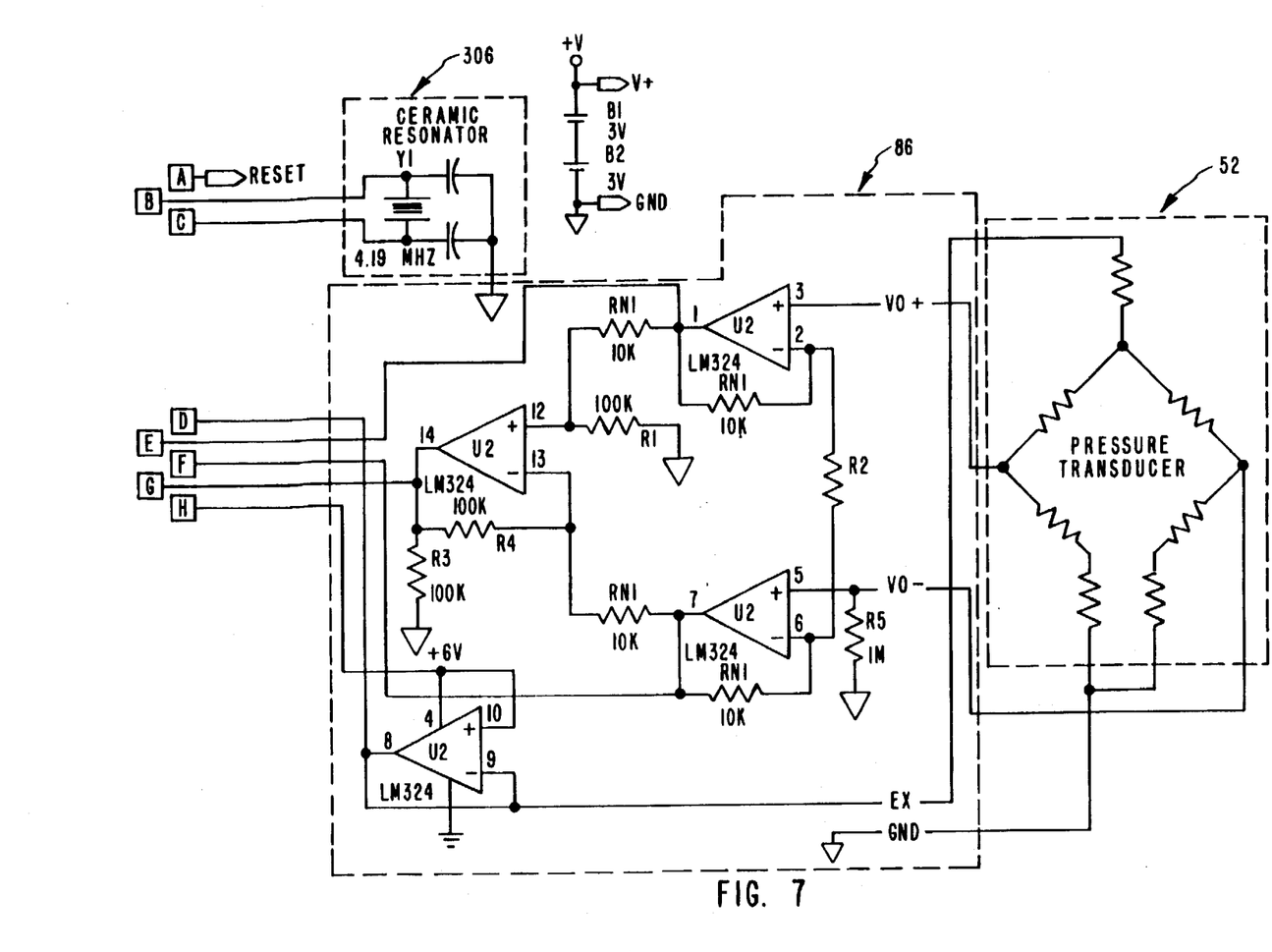

The electronic circuit means, by way of example and illustration, are detailed in reference to the functional block diagram of FIG. 5, and the accompanying electrical schematic diagram of FIGS. 6 and 7, which together illustrate one presently preferred implementation of the block diagram of FIG. 5 in its presently understood best mode.

With particular reference to FIG. 5, a transducer is shown in chip carrier member 52 and is electrically connected as schematically shown at 54. Connection 54 is made by means of cable 48 and wires 47, as described above in FIG. 2, to the circuit components which serve as an amplifier and signal conditioning circuitry 86 and also as identified by those circuit components which are enclosed within the dashed box identified by the reference numeral 86 in FIG. 7.

From amplifier and signal conditioning circuit 86, the amplified analog signal is then input as schematically represented at a line 352 to a control port 310 which is internal to the microprocessor's integrated circuitry. From control port 310 the signal is input as schematically indicated at line 314 to an analog to a digital (A/D) convertor 350 which is also internal to the microprocessor's integrated circuitry. Digital convertor 350 serves as an example of a means for converting the amplified signal from the analog to a digital form.

The particular integrated circuit which is used for microprocessor 190 is identified in FIG. 6 as integrated circuit U1. It should be appreciated that the particular circuit components and circuit design as illustrated in FIGS. 6 and 7 are intended merely as an example of the presently preferred embodiment and the presently understood best mode of implementing the overall functions which are represented by the block diagram of FIG. 5. FIGS. 6 and 7 illustrate in detail an electrical schematic diagram showing the pin numbers and interconnections for each of the integrated circuit components and the other circuit elements used in the implementation of the block diagram of FIG. 5. Of course other circuit designs could be devised that would work satisfactorily, using either software-based digital processing circuitry or hardware-based circuit designs.

With continued reference to FIGS. 5 through 7, the digital form of the signal is input as schematically indicated at line 352 to a digital processor 328. Digital processor 328 is controlled by the programmed instructions stored in a program memory (ROM) 334 and which are communicated as schematically illustrated at lines 340 through a latch 338 to digital processor 328. The particular program instructions carried out by digital processor 328 are hereinafter more fully described. The program instructions are addressed by digital processor 328 as schematically represented by the lines 340 through latch 338.

Briefly summarized, the instructions stored in program memory 334 are utilized by digital processor 328 to derive from the digitized transducer signal the non-cyclical pressure which is being exerted by tube 20 at opening 21 of the pressure port and to display the sensed pressure on display panel 66 at 196, 290, and 292. Alternatively, if the pressure is cyclical, such as that which occurs in the circulatory system of a patient, display panel 66 will reflect a derived pulse rate at 194, the systolic and diastolic pressures respectively at 290 and 292, the mean pressure at 196, and a flash of the heart symbol 198 with each pulse of the cyclical pressure. As noted above, the derivation of hemodynamic data is designed to occur in real time as the pressures are being applied.

The data memory means of the electronic circuit means is provided, as an example illustrated in the embodiment of FIG. 5, by a scratch pad random access memory (RAM) 336 which is also accessed through latch 338 by digital processor 328. RAM 336 is used to record and store the static pressure data or the cyclical hemodynamic pressure data when pressure monitor 10 is activated by depressing control button 178.

A timer 330 also communicates as schematically indicated by a line 332 with digital processor 328, and is internal to the integrated circuitry contained on microprocessor 190. Serial data receivers and drivers 344 also communicate as schematically illustrated at lines 346 and 348 with digital processor 328, and are internal to the integrated circuitry of microprocessor 190. Although not presently preferred, the serial data receivers and drivers 344 can be used for outputting a variety of data through a serial communication output/input line as schematically indicated at lines 355, 357 and 359.

An LCD driver 316, also internal to the circuitry of integrated microprocessor 190, is used to control display panel 66 as schematically indicated at a line 324. Additionally, the LED backlights 308 are controlled through control port 310 as schematically indicated at lines 312, 318 and 320. LED backlights 308 are positioned on opposite ends of display panel 66 so that the information which is digitally displayed thereon is more clearly visible by lighting opposite ends, as schematically shown at 107 in FIG. 1. Backlighting is particularly helpful in darkened environments during transportation of the patient where pressure is being monitored.

In reference to FIGS. 6 and 7, the appropriate pin connections and the identification of each corresponding integrated circuit component is illustrated in detail in the schematic diagrams of FIGS. 6 and 7 taken in conjunction with the part number identification information set forth in the aforementioned U.S. patent application Ser. No. 07/664,587, titled TOTALLY SELF-CONTAINED, DIGITALLY CONTROLLED, DISPOSABLE SYRINGE INFLATION SYSTEM, AND METHOD FOR MONITORING, DISPLAYING AND RECORDING BALLOON CATHETER INFLATION DATA, filed on Mar. 4, 1991, which was incorporated above by reference.

Power for microprocessor 190 and other circuit components is supplied by battery 192 which is also illustrated in connection with housing assembly 150 in FIGS. 2 and 3. Battery 192 advantageously permits elimination of any connecting cables or the like so that pressure monitor 10 is totally self-contained and does not require outside connection to any other power source. This advantage simplifies pressure monitor 10 and makes its use, particularly during the patient's movement from one location to another, easier.

Since pressure monitor 10 is battery operated, conservation of the batteries is important. For example, it is not uncommon for a patient to be transported or temporarily stationed on a gurney for several hours while other routines are being performed or if a hospital room is being prepared for the patient. Accordingly, to conserve the battery during extended use, microprocessor 190 is preferably programmed to go into a standby mode. Power to LED backlights 308 is turned off whenever microprocessor 190 counts them as having been on for a preselected length of time (as, for example, 20 minutes). By pushing control button 178, LED backlights 308 will be restored to light control panel 66 as shown by 107 in FIG. 1.

It is preferable that microprocessor 190 is programmed so that display panel 66 will display the indicia at "BAT", as shown at 293 in FIG. 4, when power output from battery 192 is substandard or otherwise inadequate.

In a preferred node of operation, pressure monitor 10 is turned on by depressing control button 178 once. The unit may also be turned off by pressing control button 178 a preselected number of times during a selected length of time. Preferably, pressure monitor 10 may be turned off by pressing control button 178 three times within one second.

The software controlling microprocessor 190 can be arranged so that it will be sensitive to and detect extremely high or extremely low pulse rates. For example, if the pulse rate is over 252 beats per minute or less than 15 beats per minute, then the software would cause the pulse rate display on control panel 66 to be cleared and display no value. In such a case, however, it is desirable that the device would continue to correctly measure mean pressure at digital readout 196.

When a catheter containing an incompressible fluid is in fluid communication with the circulatory system of a patient, the blood pressure thereof may be monitored. It is intended that the transducer chip of carrier member 52 will be in fluid communication with the incompressible fluid column. By so doing, the transducer senses the cyclical heartbeat of the patient as evidenced by pressures exerted upon the incompressible fluid column. When the pressure reaches its cyclical maximum peak, this is known as the systolic pressure. When the pressure reaches a minimum valley, this is known as the diastolic pressure. The systolic pressure is that pressure exerted within the circulatory system of the patient by the contraction of the heart. Conversely, the diastolic pressure is that pressure when the heart is at rest or when it is fully dilated.

The presently preferred embodiment tracks both maximum peaks and minimum valleys through a series of heartbeats. An average pressure sensed by the transducer, also known as mean arterial pressure (M.A.P.), is calculated by taking the average of a series of pressure readings over a preselected length of time, such as four seconds. The pulse rate of the patient can be calculated using the time difference between cyclical maximum pressure peaks. Preferably, this calculation is made when a new minimum valley pressure is detected after the last maximum peak pressure. The heart display 198 on display panel 66 will flash preferably at each maximum peak pressure and will turn off with each minimum valley pressure. It is preferable that the present device incorporate software to control microprocessor 190 such as to find maximum peaks and minimum valleys using software that uses a time and distance weight scheme, calculated by using running weighted averages. A preferable technique for such pressure wave form analysis is disclosed in Exhibit A in the source code included herewith.

Typical problems in blood pressure monitoring involve the existence of a bubble in the catheter line or involve an improper intracorporeal catheter placement. A bubble will cause an artificially high systolic and low diastolic pressure readings, or in other words, an overestimate of the systolic pressure and an underestimate the diastolic pressure. The phenomena is called catheter "whip" and causes the pressure wave forms to have a damping or ringing characteristic. As an additional difficulty in pressure wave form monitoring, blood pressure monitors should accurately find the maximum and minimum of each heartbeat. Many wave forms have 'pre' and 'post' peaks and valleys which should not be mistaken for the peak and valley pressure for the heartbeat.

Microprocessor 190 can be programmed to diagnose the pressures sensed to determine if there is an abnormal systolic or diastolic pressure detected during blood pressure monitoring. The software used to control the microprocessor can be designed to handle the above stated problems of pressure distortion by checking for a sharp falling off of the pressure wave form after a peak systolic reading (underdamping) and then checking for a "ringing" characteristic of the wave form. The ringing characteristic is also called the systolic "whip."

Ideally, a software diagnosis to detect for distortion caused by underdamping or catheter whip would best apply a square wave pressure to a pressure monitoring system and then look for a dampening sine wave pattern on top of the square wave. The appearance of the pressure wave form would be a sharp falling off peak with a sine wave dampening down to the real square wave level.

Detecting the presence of bubbles in a catheter line while it is connected to the patient is difficult. This is particularly true in that the wave forms are rounded and different wave form shapes are produced when measuring pressure from different places within the patient. Thus, the effect of a bubble in the system changes with the size thereof and makes it difficult to check for a sharp falling off of a peak caused by catheter whip or ringing. Depending on the wave form and the resonance of the pressure monitoring system, the overshoot of the pressure wave form may or may not happen at the top of the wave form. The overshoot could show up as a 'pre' or 'post' peak. The "ringing" characteristic will happen each time the slope of the pressure wave form changes sign, causing an abnormally high number of minor peaks and valleys.

The software used to control the microprocessor can be designed to handle the above stated problems in a great variety of methods and techniques. By way of example and not by way of limitation, one such preferred technique can be performed by establishing that the following conditions be met before a display on display panel 66 gives a visible diagnostic of a poor wave error indicator:

A. Underdamped Case—Catheter Whip/Ringing

1. If the pressure has an average of 10 or more changes in the sign of the slope per wave form, an error has occurred. The error here is the "ringing" characteristic. A change in the sign of the slope is detected by keeping the direction of the last slope, checking the current pressure reading with the last pressure reading to see if the sign of the wave form slope changes, and then incrementing a direction change counter. The software then resets the direction counter every time a new peak is found.

2. The software should observe the parameter that an average of at least one pulse in six should show pre-peaks. A pre-peak occurs when the software program records a false maximum pressure peak and then later detects the real maximum pressure peak. This condition is caused by the overshoot (sharp rise and falling off of the pressure) at the top (peak) of the wave form.

B. Overdamped Case

1. If the program detects that over half of the wave forms have no minor peaks or minor valleys, an error condition has occurred. Such an occasion would present itself when the slope of the wave forms changes sign at only the maximum peak and minimum valley. Overdamped wave forms are caused by a bubble in the catheter. The overdamping effect removes the characteristic dicrotic notch in the hemodynamic wave form.

In the case of any of the above error conditions, the microprocessor can be programmed such that display panel 66 is put into a blinking mode to indicate to the user that a poor pressure wave form is being applied to the pressure transducer. Audible alarms are also an equivalent technique.

By using a microprocessor controlled circuit, the display on display panel 66 of pulse rate, mean pressure, and blood pressure (systolic/diastolic) can be updated a frequent and preselected number of times per second by microprocessor 190 to ensure currency of hemodynamic data. For example, the updating would preferably be done four times per second.

Pressure monitor 10 may also be used to measure DC or constant pressures. For example, intrauterine pressures, abdomen insufflation pressures, intracranial pressures, intraosteal pressures, and compartmental pressures may be monitored. When pressure is constant, heart rate symbol 198 and pulse rate digital data 194 will all be blank. However, mean pressure 196 and systolic and diastolic pressures 290, 292, respectively, will all show the constant pressure that is being sensed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A totally self-contained, disposable pressure monitoring apparatus for monitoring and displaying physiological pressures of a patient that are either essentially constant intracompartmental pressures or cyclic hemodynamic pressures, comprising:

housing means for defining a transducer chamber and comprising a pressure monitoring port means for providing communication of fluid pressures to the transducer chamber;

transducer means, situated in said transducer chamber so as to be totally self-contained within said housing means and disposable therewith, for sensing said fluid pressures and for outputting an electrical signal proportional to said sensed fluid pressures, said transducer means being placed in fluid communication with said pressure monitoring port means;

electronic circuit means, electrically connected to said transducer means and mounted within said housing means so as to be totally self-contained within said housing means and disposable therewith, for receiving said electrical signals and for electronically processing said signals, said electronic circuit means comprising digital processor means programmed so as to (1) automatically derive electronic data responsive to the electrical signal sensed by said transducer means so that the derived data will represent either the cyclic hemodynamic or essentially constant intracompartmental physiological pressures of the patient, and so as to (2) automatically alter the output of a digital display responsive to the electrical signal sensed by said transducer means so that depending on whether the electronic data represent the cyclic hemodynamic pressures or the essentially constant intracompartmental pressure of the patient;

display means, electrically connected to said electronic circuit means and contained within said housing means so as to be totally self-contained within said housing means and disposable therewith, for providing a visual display of the physiological pressures of the patient, said display means responding to said electronic circuit means so as to automatically alter the output of the display so that, in the case of data representing the cyclic hemodynamic pressures, locations are provided on said display for displaying a mean pressure value, a pulse rate value, and systolic and diastolic values, and said display means responding to said electronic circuit means so as to automatically display, in the case of data representing an essentially constant intracompartmental pressure, only a constant pressure value displayed at each said location; and power means, mounted within said housing means so as to be totally self-contained within said housing means and disposable therewith, for supplying all operational electrical power to said transducer means, said electronic circuit means, and said display means.

2. An apparatus as defined in claim 1, wherein said electronic circuit means comprises:

means for amplifying said signal output by the transducer means;

means for converting said amplified signal from an analog to a digital form;

digital processor means for processing said digital form of said signal so as to derive therefrom digital data which represents the physiological pressures;

data memory means for storing the digital data derived by said digital processor means; and program memory means for storing machine-readable instructions utilized by said digital processor means to derive, store, retrieve and display said digital data.

3. A pressure monitoring apparatus as defined in claim 2, wherein said display means comprises a display panel providing a digital readout of the digital data derived by said digital processor means.

4. A pressure monitoring apparatus as defined in claim 3, further comprising switch means for selectively electrically connecting the power means to the transducer means, the electronic circuit means, and the display means.

5. A pressure monitoring apparatus as defined in claim 2, wherein:

said transducer means comprises a diaphragm that is flexed in response to the sensed fluid pressures, a front side of the diaphragm being disposed over the pressure monitoring port means, and a backside of the diaphragm in fluid communication with atmospheric or calibration pressures;

said housing means further comprises a calibration port means for providing a vent to atmosphere and for providing communication of calibration pressure to the back side of the diaphragm; and said pressure monitoring apparatus further comprises:
first hermetic sealing means for creating an airtight seal so that the front side of the diaphragm is in fluid communication only with the pressure monitoring port means and the sensed fluid pressures in the fluid passageway; and second hermetic sealing means for creating an airtight seal so that the backside of the diaphragm is in fluid communication only with the calibration port means and the atmospheric or calibration pressures communicated therethrough.

6. A pressure monitoring apparatus as defined in claim 1, wherein:

said transducer means comprises a diaphragm that is flexed in response to the sensed fluid pressures, a front side of the diaphragm being disposed over the pressure monitoring port means, and a backside of the diaphragm in fluid communication with atmospheric or calibration pressures;

said housing means further comprises a calibration port means for providing a vent to atmosphere and for providing communication of calibration pressure to the back side of the diaphragm; and said pressure monitoring apparatus further comprises:
first hermetic sealing means for creating an airtight seal so that the front side of the diaphragm is in fluid communication only with the pressure monitoring port means and the sensed fluid pressures in the fluid passageway; and second hermetic sealing means for creating an airtight seal so that the backside of the diaphragm is in fluid communication only with the calibration port means and the atmospheric or calibration pressures communicated therethrough.

7. A pressure monitoring apparatus as defined in claim 6, wherein the calibration port means comprises:

a well extending inside of the transducer chamber with a bottom and cylindrical sides, and an open top; and wherein the second hermetic sealing means comprises an elastomeric member encircling in a fluid tight manner the cylindrical sidewalls of the well inside of the transducer chamber.

8. A pressure monitoring apparatus as defined in claim 7, wherein the bottom of the well has a male projection extending therefrom, said male projection having a small hole therein for communicating therethrough the atmospheric or calibration pressures.

9. A pressure monitoring apparatus as defined in claim 1, wherein:

the electronic circuit means electronically processes said electrical signals so as to derive and so as to automatically display or record therefrom electronic data representing an error condition when there are a predetermined series of abnormal fluid pressures sensed by said transducer means; and wherein said display means outputs a visual display of the error condition.

10. A pressure monitoring apparatus as defined in claim 1, wherein:

the electronic circuit means electronically processes said electrical signals so as to derive and so as to automatically display or record therefrom electronic data representing an error condition when there are a predetermined series of abnormal fluid pressures sensed by said transducer means; and wherein said display means outputs a visual display of the error condition.

11. A totally self-contained disposable pressure monitoring apparatus for monitoring and displaying physiological pressures of a patient that are either essentially constant intracompartmental pressures or cyclic hemodynamic pressures, comprising:

housing means for defining a transducer chamber and comprising a pressure monitoring port means for providing communication of fluid pressures to the transducer chamber;

transducer means, situated in said transducer chamber so as to be totally self-contained within said housing means and disposable therewith, for sensing said fluid pressures and for outputting an electrical signal proportional to said sensed fluid pressures, said transducer means being placed in fluid communication with said pressure monitoring port means, said transducer means comprising a diaphragm that is flexed in response to the sensed fluid pressures, a front side of the diaphragm disposed over the pressure monitoring port means;

first hermetic sealing means for creating an airtight seal so that the front side of the diaphragm is in fluid communication only with the pressure monitoring port means and the sensed fluid pressures in the fluid passageway;

said housing means further comprising a calibration port means for providing a vent to atmosphere and for providing communication of calibration pressure to the transducer means;

said transducer means further comprising a backside of the diaphragm in fluid communication with the atmospheric or calibration pressures communicated through the calibration port means;

second hermetic sealing means for creating an airtight seal so that the backside of the diaphragm is in fluid communication only with the calibration port means and the atmospheric or calibration pressures communicated therethrough;

electronic circuit means, electrically connected to said transducer means and mounted within said housing means so as to be totally self-contained within said housing means and disposable therewith, for receiving said electrical signals and for electronically processing said signals, said electronic circuit means comprising digital processor means programmed so as to (1) automatically derive electronic data responsive to the electrical signal sensed by said transducer means so that the derived data will represent either the cyclic hemodynamic or essentially constant intracompartmental physiological pressures of the patient, and so as to (2) automatically alter the output of a digital display responsive to the electrical signal sensed by said transducer means so that depending on whether the electronic data represent the cyclic hemodynamic pressures or the essentially constant intracompartmental pressure of the patient;

display means, electrically connected to said electronic circuit means and contained within said housing means so as to be totally self-contained within said housing means and disposable therewith, for providing a visual display of the physiological pressures of the patient, said display means responding to said electronic circuit means so as to automatically alter the output of the display so that, in the case of data representing the cyclic hemodynamic pressures, locations are provided on said display for displaying a mean pressure value, a pulse rate value, and systolic and diastolic values, and said display means responding to said electronic circuit means so as to automatically display, in the case of data representing an essentially constant intracompartmental pressure, only a constant pressure value displayed at each said location; and power means, mounted within said housing means, for supplying all operational electrical power to said transducer means, said electronic circuit means, and said display means.

12. An apparatus as defined in claim 11, wherein said electronic circuit means comprises:

means for amplifying said signal output by the transducer means;

means for converting said amplified signal from an analog to a digital form;

digital processor means for processing said digital form of said signal so as to derive therefrom digital data which represents the monitored physiological pressures;

data memory means for storing the digital data derived by said digital processor means; and program memory means for storing machine-readable instructions utilized by said digital processor means to derive, store, retrieve and display said digital data.

13. A pressure monitoring apparatus as defined in claim 12, wherein said display means comprises a digital readout of the digital data derived by the digital processor means.

14. A pressure monitoring apparatus as defined in claim 11, further comprising switch means for selectively electrically connecting the power means to the transducer means, the electronic circuit means, and the display means.

15. A pressure monitoring apparatus as defined in claim 11, wherein the calibration port means comprises:

a well extending inside of the transducer chamber with a bottom and cylindrical sides, and an open top; and wherein the second hermetic sealing means comprises an elastomeric member encircling in a fluid tight manner the cylindrical sidewalls of the well inside of the transducer chamber.

16. A pressure monitoring apparatus as defined in claim 15, wherein the bottom of the well has a male projection extending therefrom, said male projection having a small hole therein for communicating therethrough the atmospheric or calibration pressures.

17. A pressure monitoring apparatus as defined in claim 11, wherein:

the electronic circuit means electronically processes said electrical signals so as to derive and so as to automatically display or record therefrom electronic data representing an error condition when there are a predetermined series of abnormal fluid pressures sensed by said transducer means; and wherein the display means outputs a visual display of the error condition.

18. A totally self-contained, disposable pressure monitoring apparatus for monitoring and displaying physiological pressures of a patient that are either essentially constant intracompartmental pressures or cyclic hemodynamic pressures, comprising:

housing means for defining a transducer chamber and comprising a pressure monitoring port means for providing communication of fluid pressures to the transducer chamber;

a transducer means, situated in said transducer chamber so as to be totally self-contained within said housing means and disposable therewith, for sensing said fluid pressures and outputting an electrical signal proportional to said sensed fluid pressures, said transducer means being placed in fluid communication with said pressure monitoring port means;

electronic circuit means, electrically connected to said transducer means and mounted within said housing means so as to be totally self-contained within said housing means and disposable therewith, for receiving said electrical signals and for electronically processing said signals so as to (1) automatically derive electronic data responsive to the electrical signal sensed by said transducer means so that the derived data will represent either the cyclic hemodynamic or essentially constant intracompartmental physiological pressures of the patient, and so as to (2) automatically alter the output of a digital display responsive to the electrical signal sensed by said transducer means so that depending on whether the electronic data represent the cyclic hemodynamic pressures or the essentially constant intracompartmental pressure of the patient, said electronic circuit means comprising:

means for amplifying said signal output by the transducer means;

means for converting said amplified signal from an analog to a digital form;

digital processor means for processing said digital form of said signal so as to derive therefrom digital data which represents the monitored physiological pressures;

data memory means for storing the digital data derived by said digital processor means; and program memory means for storing machine-readable instructions utilized by said digital processor means to derive, store, retrieve and display said digital data; and display means, electrically connected to said electronic circuit means and contained within said housing means so as to be totally self-contained within said housing means and disposable therewith, for providing a visual display of the physiological pressures of the patient, said display means responding to said electronic circuit means so as to automatically alter the output of the display so that, in the case of data representing the cyclic hemodynamic pressures, locations are provided on said display for displaying a mean pressure value, a pulse rate value, and systolic and diastolic values, and said display means responding to said electronic circuit means so as to automatically display, in the case of data representing an essentially constant intracompartmental pressure, only a constant pressure value displayed at each said location; and power means, mounted within said housing means, for supplying all operational electrical power to said transducer means, said electronic circuit means, and said display means.

19. A pressure monitoring apparatus as defined in claim 18, wherein:

said transducer means comprises a diaphragm that is flexed in response to the sensed fluid pressures, a front side of the diaphragm being disposed over the pressure monitoring port means, and a backside of the diaphragm in fluid communication with atmospheric or calibration pressures;

said housing means further comprising a calibration port means for providing a vent to atmosphere and for providing communication of a calibration pressure to the back side of the diaphragm; and said pressure monitoring apparatus further comprises:
first hermetic sealing means for creating an airtight seal so that the front side of the diaphragm is in fluid communication only with the pressure monitoring port means and the sensed fluid pressures in the fluid passageway; and second hermetic sealing means for creating an airtight seal so that the backside of the diaphragm is in fluid communication only with the calibration port means and the atmospheric or calibration pressures communicated therethrough.

20. A pressure monitoring apparatus as defined in claim 19, wherein the calibration port means comprises:

a well extending inside of the transducer chamber with a bottom and cylindrical sides, and an open top; and the second hermetic sealing means comprises an elastomeric member encircling in a fluid tight manner the cylindrical sidewalls of the well inside of the transducer chamber.

21. A pressure monitoring apparatus as defined in claim 20, wherein the bottom of the well has a male projection extending therefrom, said male projection having a small hole therein for communicating therethrough the atmospheric or calibration pressures.

22. A totally self-contained, disposable pressure monitoring apparatus for monitoring and displaying comprising;

a housing means for defining a transducer chamber and comprising a pressure monitoring port means for providing communication of fluid pressures to the transducer chamber;

a piezoresistive semiconductor transducer, mounted in said transducer chamber so as to be totally self-contained within said housing means and disposable therewith, in fluid communication with said fluid pressures in the fluid passageway through the pressure monitoring port, said transducer generating an electrical signal proportional to the sensed fluid pressure; and a controller mounted within said housing means so as to be totally self-contained within said housing means and disposable therewith, and electrically connected to said transducer, said controller comprising:

means for amplifying said signal output by said transducer;

means for converting said amplified signal from an analog to a digital form;

processor means for processing said digital form of said signal so as to electronically monitor and automatically display either (1) in the case of hemodynamic pressure, a mean pressure value, a pulse rate value, and systolic and diastolic values, or (2) in the case of an essentially constant intracompartmental pressure, only a constant pressure value by performing the steps of:

deriving data from said digital signals which represents a numerical value of either (a) the systolic pressure, diastolic pressure, mean pressure and pulse rate or an essentially constant pressure value;

electronically storing all said derived data; and automatically displaying said numerical values for either said case in a visually perceptible manner to a system user;

data memory means for storing the digital data derived by said digital processor means;

program memory means for storing machine-readable instructions utilized by said digital processor means to perform said steps;

display means for automatically providing in the case of hemodynamic pressure, a mean pressure value, a pulse rate value, and systolic and diastolic values, and, and for automatically providing in the case of an essentially constant intracompartmental pressure, only a constant pressure value; and power means for supplying electrical power to said piezoresistive semiconductor transducer and said controller.

23. A pressure monitoring apparatus as defined in claim 22, wherein:

said piezoresistive semiconductor transducer comprises a diaphragm that is flexed in response to the sensed fluid pressures, a front side of the diaphragm being disposed over the pressure monitoring port means, and a backside of the diaphragm in fluid communication with atmospheric or calibration pressures;

said housing means further comprising a calibration port means for providing a vent to atmosphere and for providing communication of calibration pressure to the back side of the diaphragm; and wherein said pressure monitoring apparatus further comprises:

first hermetic sealing means for creating an airtight seal so that the front side of the diaphragm is in fluid communication only with the pressure monitoring port means and the sensed fluid pressures in the fluid passageway; and second hermetic sealing means for creating an airtight seal so that the backside of the diaphragm is in fluid communication only with the calibration port means and the atmospheric or calibration pressures communicated therethrough.

24. A pressure monitoring apparatus as defined in claim 23, wherein the female calibration port means comprises:

a well extending inside of the transducer chamber with a bottom and cylindrical sides, and an open top; and wherein the second hermetic sealing means comprises an elastomeric member encircling in a fluid tight manner the cylindrical sidewalls of the well inside of the transducer chamber.

25. A pressure monitoring apparatus as defined in claim 24, wherein the bottom of the well has a male projection extending therefrom, said male projection having a small hole therein for communicating therethrough the atmospheric or calibration pressures.

* * * * *

UNITED STATES PATENT AND TRADEMARK OFFICE
CERTIFICATE OF CORRECTION

PATENT NO. : 5,711,302

DATED : January 27, 1998

INVENTOR(S) : Fred P. Lampropoulos; Don C. Kartchner; Steven R. Taylor

It is certified that error appears in the above-identified patent and that said Letters Patent is hereby corrected as shown below:

Col. 8, line 66, after "adhesive" change "66" to --67--

Signed and Sealed this

Eighth Day of September, 1998

Attest:

BRUCE LEHMAN

Attesting Officer      Commissioner of Patents and Trademarks